United States Patent [19]

Pratt, Jr. et al.

[11] 4,283,799
[45] Aug. 18, 1981

[54] PRE-COATED BODY IMPLANT

[75] Inventors: George W. Pratt, Jr., Wayland; Robert Poss, Marblehead; Jeremy K. Chung, Cambridge, all of Mass.

[73] Assignee: Massachusetts Institute of Technology, Cambridge, Mass.

[21] Appl. No.: 73,834

[22] Filed: Sep. 10, 1979

[51] Int. Cl.³ ............................ A61F 1/00; A61F 1/03
[52] U.S. Cl. ........................................ 3/1.913; 3/1.9; 128/92 C
[58] Field of Search ............... 3/1.9, 1.913; 128/92 C, 128/92 CA; 433/175

[56] References Cited

U.S. PATENT DOCUMENTS

| 3,713,860 | 1/1973 | Auskern | 3/1.9 X |
|---|---|---|---|
| 3,790,507 | 2/1974 | Hodosh | 3/1.9 X |
| 4,051,598 | 10/1977 | Sneer | 433/175 |
| 4,131,597 | 12/1978 | Bluethgen et al. | 3/1.9 X |
| 4,202,055 | 5/1980 | Reiner et al. | 3/1.913 X |

Primary Examiner—Clifford D. Crowder
Attorney, Agent, or Firm—Arthur A. Smith, Jr.; Thomas J. Engellenner

[57] ABSTRACT

A pre-coated body implant, such as, for example, a hip prosthesis, in which that portion of the implant that attaches to or is inserted into a skeletal member of the body has a pre-coating of a material (e.g., an acrylic material) covering all or most of said portion and bonded thereto.

4 Claims, 5 Drawing Figures

PRE-COATED BODY IMPLANT

The present invention relates to bone implants and the like.

A very severe problem with regard to bone implants is the tendency of such implant to become loose or, indeed, to be loose even at the time of implantation. Currently in the United States approximately ten percent of the population reportedly has discernible symptoms of arthritic disease. Despite the lesser mortality rate than that of heart disease and cancer, this form of disability creates tremendous psychological physical and economic impact on the patients because of pain and functional impairments incurred. The consequent loss of manpower and increase in health care expenses are substantial. Thus, rehabilitation of damaged joints is of great concern to the social and economic well-being of the community. Recent advances in the field of total-hip arthroplasty have given much optimism to the improvement of clinical management in this area, and brought promise of relief from hip pain, improved gait, and a satisfactory range of motion. Successful replacement surgery depends heavily on the clinical expertise of an experienced and artistic surgeon as well as on the proper designs of clinical prostheses, many of which now in use, unfortunately, are still classified as experimental devices, some one hundred types in all. Until accurate information on the biomechanical behavior of the system is known, complications of such surgery will inevitably arise such as loosening of the femoral prosthesis. Loosening is the most prevalent long-term complication of total-hip arthroplasty. An imbalance of the distribution of forces carried by surrounding soft tissues caused by pathological alteration will strain the joint to develop deformation, which in turn leads to eventual loosening. There are other factors that could induce loosening, which will be discussed in more detail. When loosening occurs in the absence of infection, the femur is almost always affected. Once firm fixation is lost, loosening is usually progressive. Breakage of bone and/or prosthesis will result, which could lead to life-long disability. It has been shown that even the slightest amount of loosening can be of critical importance in producing high stress levels in the prosthesis stem and that rigid fixation of the entire stem is essential. It has also been observed that movement during surgery can easily occur, thereby enhancing the possibility of eventual loosening. The introduction of acrylic cement to achieve rigid fixation of metal and plastic prosthesis to bone twenty years ago revolutionized arthroplasty. Bone-cement made of polymethyl methacrylate is introduced into the medullary canal between the prosthesis stem and the inner aspect of the femur. This layer of bone-cement enables distribution of impressed load over a larger area than would otherwise be the case. The bone structure when stressed must deform. If no overstressing or local stress concentrations are to occur, the bone must be allowed to deform in its natural way. Therefore, the only manner for accommodating this is by utilizing an intermediate layer of an elastic substance whose Young's modulus is lower than that of the implant and that of the bone. Polymethyl methacrylate satisfies such requirements.

Success of implant fixation depends largely on mechanisms of the interfaces. Therefore, it is appropriate to study the mechanical structure at the interfaces.

Between cement and bone tissue there is no real adhesion. The mechanical strength of the bond between the two materials derives its strength from the action of interdigitation. To prepare the cement bed in bone, part of the spongiosa is removed. This leaves an irregular surface, characterized by projecting, broken-off spongiosa ridges with marrow still located at the bottom of the recesses. By forcing the prosthesis stem mechanically, the cement is forced into these recesses and surrounds the spongiosa trabeculae. Owing to the shrinkage of the cement in curing and cooling (about 4% in volume), the more or less hardened cement may withdraw somewhat from the surrounding spongiosa.

The inside of the upper half of the femoral shaft is generally covered with a more or less marked spongiosa layer, which is formed by sheets of spongiosa running circularly. Here the anchorage is as good as in the spongiosa of the trochanter. Only where the cortex is exposed in the femur is keying no longer possible in the manner described. The cement does not hold onto smooth surfaces, and, owing to the volumetric shrinkage during cooling, the cement filling contracts somewhat, so that it fits loosely inside a smooth bone tube.

Turning now to the prothesis/cement interface which is crucial in this disclosure, the acrylic bone-cement does not adhere very firmly either to the usual socket plastics or to metals. Accordingly, firm fixation of the prosthesis in the cement can be achieved only by mechanical keying. Prosthesis metals have a coefficient of cubical expansion about three times lower than that of the acrylic cement. Consequently, during thermal contraction in the course of cement in-situ polymerization, the prosthesis stem surrounded by cement shrinks less than the cement, so that the latter tightens its grip. It should be clearly understood that the cement to implant (here the hip prosthesis) bond is one of mechanical gripping not a chemical adhesion. This bond is much more subject ot faulty implantation in the actual operating room situation than the bond that can be achieved between old hardened cement and new cement that cures on the surface of an already cured cement layer. In considering the pathogenesis of loosening of prosthetic components it may be helpful to examine closely factors that are conducive to the loosening of prosthetic components.

Faulty implantation is often a surgical error caused by varus positionings of prosthesis, improper curing of cement, insufficient amount of cement used, or movements incurred during surgery. Varus positioning of prosthesis has been described earlier. Lack of monomer of the acrylic cement during curing process due to, for example, excessive amounts of the monomer being dissolved in the surrounding adipose tissue during polymerization can occur. The strength of the cement thus formed will be greatly degraded and would not be able to sustain much shear stress at the interface. An insufficient amount of cement will produce voids inside the medullary canal and give rise to local stress concentration, which in turn will cause eventual loosening.

In most general terms, polymers change from rubber-like to glass-like behavior as the temperature is lowered. In the glassy state at low temperatures one would expect the stiffness to relate to the stored elastic energy on deformation which are associated with small displacements of the molecules from their equilibrium positions. In the rubbery state, on the other hand, at high temperatures, the molecular chains have considerable flexibility; so in the deformed state they can adopt conformations which lead to maximum entropy, or, more strictly, minimum free energy. The rubber-like elastic deformations are then related to changes in molecular conformations. The ease with which the polymer can jump from one conformation to another is often described by the so-called jump frequency. Accordingly, the rate of polymerization will increase with the ambient temperature at the time of mixing.

Polymers, such as poly methyl methacrylate, are usually described as viscoelastic materials, a generic term which emphasizes their intermediate position between viscous liquid and elastic solids. At low temperatures, a polymer may be glass-like with a Young's modulus of $10^{10}$–$10^{11}$ dyne/cm$^2$, whereas at high temperatures, the same polymer may be rubber-like with a Young's modulus of $10^7$–$10^8$ dyne/cm$^2$. At still higher temperatures, permanent deformation occurs under load, and the polymer behaves like a viscous liquid.

In an intermediate temperature, commonly called the glass-transition range, the polymer is neither glassy nor rubbery. It shows an intermediate modulus, is viscoelastic and may dissipate a considerable amount of energy on being strained. The glass transition manifests itself in several ways, for example by a change in the volume coefficient of expansion, which can be used to define a glass-transition temperature $T_g$.

The large difference in the volume coefficients of expansion between the prosthesis and bone-cement during surgery can be explained by the arguments of free volume, which is defined as the difference between the total volume of the material and the actual volume occupied by the molecules. As the temperature is lowered, the prosthesis, being a hard solid with negligable viscous behavior, can contract only by way of decreasing the amplitudes of vibration of the molecules about their equilibrium positions. In the course of curing cement in the rubbery state, however, there are packets of free volume, or holes too large to be lost by the mere decrease in vibration amplitudes of the molecules. If these holes are to be modified so as to conform to the equilibrium state of the material when the temperature is lowered, molecules or molecular segments must move over fairly long distances in order to accomplish this. When the jump frequency is high, as is the case for the curing cement, this re-arrangement will be almost instantaneous, and the material will assume its new equilibrium volume soon after the temperature is changed. Consequently, the contraction of the cement is more significant than that of the prothesis.

Occasionally, in current practice, a prosthesis is changed by simply removing the old prosthesis and putting a new one in its place, that is of the same size. This practice is attractive because removal of cement is difficult and often dangerous. Therefore, it would seem advantageous to re-insert a prosthesis in the intact cement bed. However, study by the present inventors shows that the quality of the bond between prosthesis and the already cured cement is not optimal and that partial re-cementing at least is preferable.

It has been possible to measure the strength of the mechanical coupling of an implant such as a hip prosthesis to the bone by mechanically exciting the composite bone-cement implant system and measuring the frequencies of the mechanical resonances. This method, known as the sonic probe technique, disclosed in an application for Letters Patent Ser. No. 026,462, filed Apr. 2, 1979 (Babyn et al), shows that a strong mechanical coupling between the implant and the bone harboring the implant results in a significant displacement of the resonant frequencies of the implant and of the bone from their pre-cemented or pre-bonded condition. The present inventors have made the important observation that the mechanical resonance frequencies of a re-cemented composite implant system remain virtually the same as that of the previously cemented system. This indicates that the coupling between the old and new cement masses by means of chemical bonding is very strong. Furthermore, a discontinuity of physical properties across the old cement/new cement interface may not be present, which is very likely as polymethyl methacrylate is an amorphous polymer. Accordingly, it is highly advantageous to employ chemical bonding between components during surgery rather than the traditional mechanical keying at the bone/cement and prosthesis/cement interface. This can be accomplished by pre-coating the femur and/or the prosthesis with bone-cement before the actual operation and then uniting the two components by in-situ polymerization of additional fresh bone-cement during surgery. Pre-coated components ensures maximum mechanical coupling at the implant/cement interface which can be prepared controllably and reproducibly pre-operatively, thus shifting the emphasis at the time of surgery to the cement/cement and cement/bone interfaces. Since the quality of chemical bonding is less susceptable to external disturbance than mechanical bonding during in-situ cement polymerization, the incidence of loosening due to movements during surgery would drastically be reduced. Furthermore, appropriate engineering and processing procedures can be employed to produce a layer of prebonded cement with the desired mechanical properties and devoid of bubbles and other defects pre-operatively on the surface of the femoral component. Another factor that can be controlled in a pre-coated implant is the modulus of elasticity of the cement pre-coating. The metal implant will have a Young's Modulus typically 10 times higher than the cement that grips the implant. Thus at the implant-cement interface there is a discontinuity in stiffness. The greater this discontinuity, the greater will be the displacement of one surface relative to the other at the interface when the composite system is subjected to a mechanical load. By curing the cement in the implant coating under special conditions of temperature, pressure or by altering the composition of the cement pre-coating it would be possible to produce a coating with elastic modulus intermediate between the metal of the implant and the cement as installed by the surgeon. This would produce a less abrupt discontinuity in elastic modulus from the implant into the bulk of the cement and would decrease the relative motion between the implant and the cement in which it is embedded. An even better tapering of elastic modulus from the implant into the cement could be achieved by loading the cement used in the pre-coating with a filler such as graphite fibers or glass fibers. Such gradual tapering of the elastic properties from the implant into the cement and in fact to the surrounding bone would produce a system which would have a minimum relative motion between different surfaces. This control of the relative motion would minimize the loosening due to mechanical loads. Corrugated surfaces on precoated cement layers would allow superior cement/cement bonding as well as quicker rate of heat dissipation during polymerization, which would imply faster rate and more complete polymerization. Furthermore, effects of the methyl methacrylate monomer vapor and heat liberated during polymerization in surgery will be greatly reduced as the femur is protected by a cement layer initially. Also, varus positioning of the prosthesis will be minimized as now the prosthesis has at least some bone-cement surrounding it.

Accordingly, it is a principal object of the present invention to provide an implant that shall overcome the above mentioned problems.

These and still further objects are addressed hereinafter.

The foregoing objects are achieved, generally, in a precoated body implant that includes, in combination, a structural member having a portion that is adapted to bond mechanically to a skeletal member of the body; and a cement pre-coating covering at least a substantial part of said portion of the structural member, which cement pre-coating clings to said portion. When the implant is installed in a patient a similar cement may be used in the bond cavity.

Figure 1:
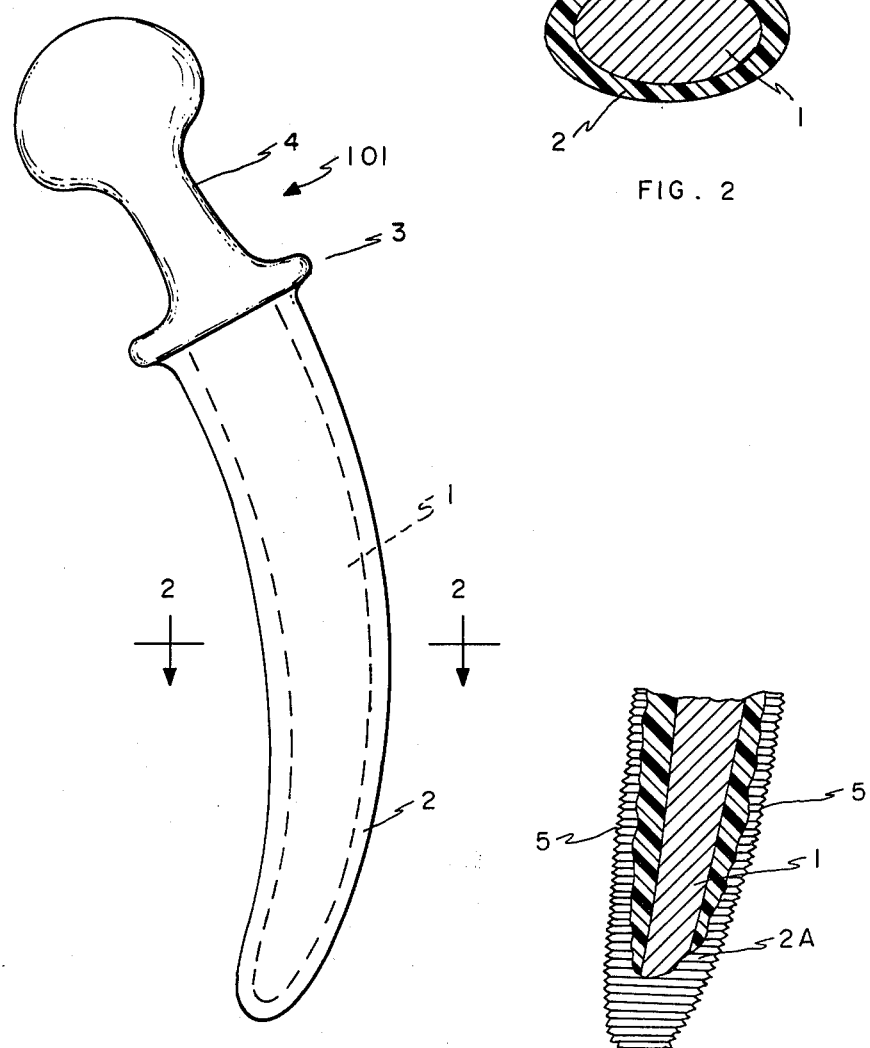
FIG. 1 is an isometric view of a pre-coated body implant.

Turning now to FIG. 1, the implant labeled 101 therein will be recognized as a prosthesis used in hip implant applications. A prosthesis of the type shown most generally is formed of metals such as stainless steel, cobalt-chromium, alloys e.g., (Vitallium) with only slight irregularities to aid cement fixation. The implant 101 has a stem 1, a shoulder 3, and a ball 4. As is known, the stem 1, when implanted in a body, is received by a cavity formed by a physician in the femur of a patient. The cavity is reamed to a size sufficient to receive the stem 1 and a volume of a doughy cement (e.g., methymethacrylate, referred to as "MMA"). Ideally, the bone cavity should be free of blood and be dry so that no blood or other fluid interferes with grouting achieved by the cement to the bone or prosthesis. The inserted prosthesis is held in place by the operating physician until polymerization of the MMA is complete; no motion of the prosthesis should take place during the period of approximately ten to fifteen minutes it takes for polymerization to occur. (See said application for Letters Patent Ser. No. 026,462, Babyn et al, filed Apr. 2, 1979 for a further discussion).

In the usual installation, the implant 101, originally has a stem 1 which is shiny metal (usually Vitallium) and which fills that portion of the bone cavity not taken up by a cement. The implant 101 when installed in a femur is held there mostly by frictional interaction between the MMA and the femur at one bonding region and between the MMA and the implant at the other bonding region. The ideas herein are intended to strengthen the cement-to-implant bond which is a region that can loosen and fail, as previously noted herein.

In current practice, after the femoral canal is prepared, cement in the doughy stage introduced. Despite the best attempts to keep the canal dry during this phase there is inevitably some admixture of blood and fat with the cement. After the maximum amount of cement has been introduced into the canal, the metal prosthesis is inserted into the cement. Ideally, the position of the prosthesis is not changed either during or after insertion so that no ridges or voids are formed at the metal-cement interface. Current practice is to introduce the cement and prosthesis as early in the polymerization process as possible to avoid ridges or voids caused by motion of the prosthesis in a more doughy or viscous cement. Post operative x-ray measurements show that a thickness of cement varying from essentially 0 to 1 centimeters can be achieved.

Data derived by the sonic probe technique disclosed in said application Ser. No. 026,462, suggest that currently employed clinical methods of assessing the completion of polymerization of bone cement is erroneous; i.e., an implant may be moved prior to complete cement polymerization causing micromotion of the completed prosthesis in its cement bed and perhaps inducing future loosening. While current techniques have been improved so that a better cement-bone interface is being achieved, it is still likely that a sub-optimal bond of prosthesis to cement is achieved, usually because of inadvertant motion of the prosthesis while the cement is polymerizing.

Figure 2:
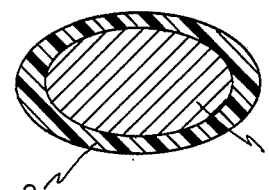
FIG. 2 is a section view, slightly enlarged, taken upon the line 2—2 in FIG. 1 and looking in the direction of the arrows.

In accordance with the present teaching, a pre-coating 2 in FIGS. 1 and 2 of MMA or some other acrylic or other material is applied to the stem 1 of the prosthesis. Experience indicates a layer 2 of about 3–5 millimeters in thickness (but not necessarily uniform) to be adequate for present purposes since a study of patients that have loose prostheses shows that a prosthesis stem which occupies fifty percent of the femoral canal has less chance of loosening than a thinner stem. Also, as above indicated, the bond between the stem 1 and the pre-coating 2 is a mechanical bond which is achieved to a great degree by shrinkage of the pre-coating 2 upon curing; hence the pre-coating 2 must be thick enough to provide adequate tensile strength to assure that mechanical bond.

Figure 3:
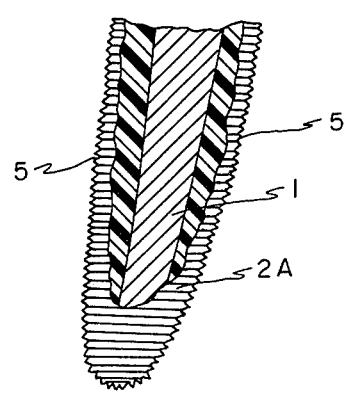
FIG. 3 is a view like that in FIG. 2 but of a modification of the implant of FIG. 2.
Figure 4:
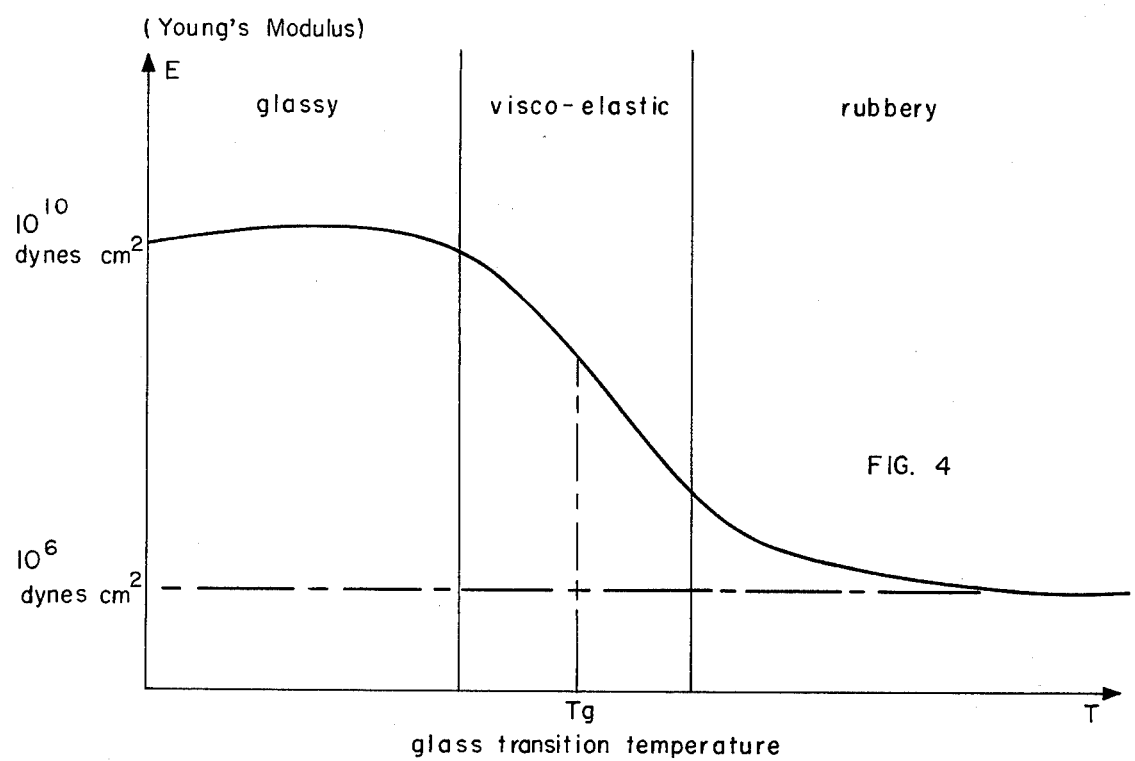
FIG. 4 is a graph showing the Youngs modulus of methylmethacrylate, (a material that may be used as the pre-coating on the implant in FIG. 1). as a function of absolute temperature.
Figure 5:
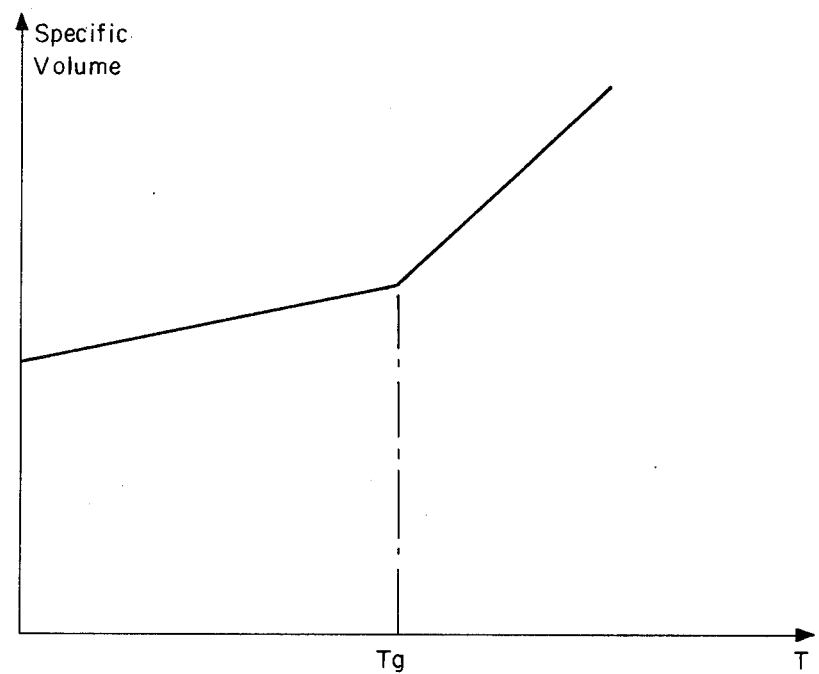
FIG. 5 is a graph showing specific volume as a function of absolute temperature for that same material.

A number of salutary consequences flow from the use of a pre-coating implant in accordance with the present invention, as now discussed. A pre-coating in a metal prosthesis of optimum thickness ensures that there will be no prosthesis-bone contact in the event of improper prosthesis, positioning, that is, the prosthesis will enjoy at least some cement covering and of optimal thickness. A pre-coating can be provided with irregularities (see the ridges on other irregularities marked 5 in the pre-coating labeled 2A in FIG. 3), thus increasing the contact area of cement-cement in the implant to provide a better mechanical and/or chemical bond. Irregularities cannot be provided in the metal stem 1 because they would result in concentrated stress which could lead to failure of that stem. The thickness of the pre-coating or layer 2 can be optimized, thereby reducing the amount of polymerized (doughy) cement introduced into the bone during implantation, and therefore the circulation would be less. It is felt on the basis of other reports that decreased exposure to monomer is desirable. Also, by increasing the mass of the prosthesis with a polymerized cement layer, better compaction of the doughy cement into the interstices of cancellous bone can be achieved, i.e., a larger stem acts as a plunger forcing doughy cement under high pressure into cancellous bone. By prepolymerization in a quality controlled setting a better bond can be achieved; e.g., a varying of the temperature of polymerization and cooling can be employed to effect better bonding of cement-to-metal if greater contraction of cement can be achieved (see FIGS. 4 and 5). The pre-coating can be applied in such a way that the elastic modulus of the coating takes on a value or range of values intermediate between the implant and the cement inserted during actual surgery. This gradation in stiffness will decrease the relative motion due to mechanical loading. Also, such problems as blood clot or fluid forming on the interface between cement and prosthesis is obviated.

The method of implanting a prosthesis into a skeletal member of a human in accordance with the present invention comprises: preparing a cavity in the skeletal member to receive the prosthesis which comprises a stem that is introduced into said cavity, covering the surface of the cavity with a cement coating, applying a cement pre-coating to said stem prior to insertion in said cavity, permitting the cement both in the cavity and on the stem to cure, applying a further quantity of the cement in a doughy condition into the cavity and, while cement is doughy introducing the stem into the cavity.

Further modifications of the invention herein disclosed (e.g., successive layers of pre-coating material) will occur to persons skilled in the art and all such modifications are deemed to be within the spirit and scope of the invention as defined by the appended claims.

What is claimed is:

1. A method of implanting a prosthesis into a skeletal member of a human, that comprises: preparing a cavity in the skeletal member to receive the prosthesis which comprises a stem that is introduced into said cavity, covering the surface of the cavity with a cement coating, applying a cement pre-coating to said stem prior to insertion into said cavity, permitting the cement both in the cavity and on the stem to cure, applying a further quantity of the cement into the cavity and introducing the stem into the cavity.

2. The method of claim 1 wherein the method further comprises the step of shaping the outer surface of the cement precoating after the precoating is applied so as to enhance bonding and positioning of the prosthesis upon introduction of the stem into the cavity.

3. The method of claim 1 wherein the step of applying a cement pre-coating to the prosthesis stem further comprises applying a pre-coating having an elastic modulus intermediate that of the stem and that of the cement which is applied to fill the cavity.

4. The method of claim 1 wherein the step of applying a cement pre-coating to the prosthesis stem further comprises applying a thin methylmethacrylate cement pre-coating to the prosthesis stem.

* * * * *